(12) United States Patent
Stillman et al.

(10) Patent No.: US 11,590,308 B2
(45) Date of Patent: Feb. 28, 2023

(54) ANESTHETIC GAS SCAVENGING AND SANITARY BREATHING TUBE SECURING DEVICE

(71) Applicants: Richard I Stillman, Mountain Lakes, NJ (US); Jordan D Stillman, Mountain Lakes, NJ (US)

(72) Inventors: Richard I Stillman, Mountain Lakes, NJ (US); Jordan D Stillman, Mountain Lakes, NJ (US)

( * ) Notice: Subject to any disclaimer, the term of this patent is extended or adjusted under 35 U.S.C. 154(b) by 391 days.

(21) Appl. No.: 16/856,289

(22) Filed: Apr. 23, 2020

(65) Prior Publication Data

US 2021/0290880 A1    Sep. 23, 2021

Related U.S. Application Data

(60) Provisional application No. 62/992,877, filed on Mar. 20, 2020.

(51) Int. Cl.
| | | |
|---|---|---|
| *A61M 16/04* | (2006.01) | |
| *A61M 16/10* | (2006.01) | |
| *A61M 16/06* | (2006.01) | |

(52) U.S. Cl.
CPC .... *A61M 16/0488* (2013.01); *A61M 16/0463* (2013.01); *A61M 16/0666* (2013.01); *A61M 16/0688* (2014.02); *A61M 16/104* (2013.01); *A61M 2202/0241* (2013.01)

(58) Field of Classification Search
CPC .......... A61M 16/0461; A61M 16/0488; A61M 16/0666; A61M 16/0688; A61M 16/0463; A61M 16/01; A61M 16/009; A61M 16/0497; A61M 2201/0241
See application file for complete search history.

(56) References Cited

U.S. PATENT DOCUMENTS

| | | | | |
|---|---|---|---|---|
| 4,328,797 A * | 5/1982 | Rollins, III | ........... | A61M 16/06 128/912 |
| 5,038,778 A * | 8/1991 | Lott | ....................... | A61M 25/02 128/DIG. 26 |
| 5,868,132 A * | 2/1999 | Winthrop | ............... | A61M 25/02 128/207.14 |
| 6,196,223 B1 * | 3/2001 | Belfer | ................ | A61M 16/0616 128/206.25 |
| 6,237,596 B1 * | 5/2001 | Bohmfalk | ........... | A61M 16/106 128/911 |
| 7,331,348 B1 * | 2/2008 | Beevers | ............ | A61M 16/0666 128/207.18 |
| 9,004,072 B2 * | 4/2015 | Barker | .............. | A61M 16/0672 128/207.18 |
| 9,302,064 B2 * | 4/2016 | Hussain | ................. | A61B 5/097 |
| 11,020,557 B1 * | 6/2021 | Lehman | ................. | A61B 5/082 |

(Continued)

*Primary Examiner* — Colin W Stuart
*Assistant Examiner* — Douglas Y Sul
(74) *Attorney, Agent, or Firm* — H. Jay Spiegel

(57) ABSTRACT

A sanitary device for securing a breathing tube to a patient during anesthesia administration, which also prevents leaking anesthetic gases from entering the operating room environment. The novel design allows rapid application by the user and prevents potential transmission of infectious agents to the patient while securing the breathing tube. A unique, integrated suction system efficiently evacuates leaking anesthetic gases. The device may be manufactured inexpensively and is provided in sanitary packaging. It is intended for single use.

16 Claims, 8 Drawing Sheets

(56) References Cited

U.S. PATENT DOCUMENTS

| | | | | |
|---|---|---|---|---|
| 2001/0016698 A1* | 8/2001 | Lloyd | ................... | A61F 15/004 |
| | | | | 602/3 |
| 2004/0182396 A1* | 9/2004 | Dennis | ................... | A62B 18/02 |
| | | | | 128/205.25 |
| 2008/0173310 A1* | 7/2008 | Marcoe | ............ | A61M 16/0497 |
| | | | | 128/207.17 |
| 2012/0330111 A1* | 12/2012 | Borody | ............ | A61M 16/0488 |
| | | | | 600/300 |
| 2013/0172768 A1* | 7/2013 | Lehman | ................ | A61M 16/06 |
| | | | | 128/205.25 |
| 2014/0366890 A1* | 12/2014 | Tao | ..................... | A61M 16/009 |
| | | | | 128/849 |

* cited by examiner

40

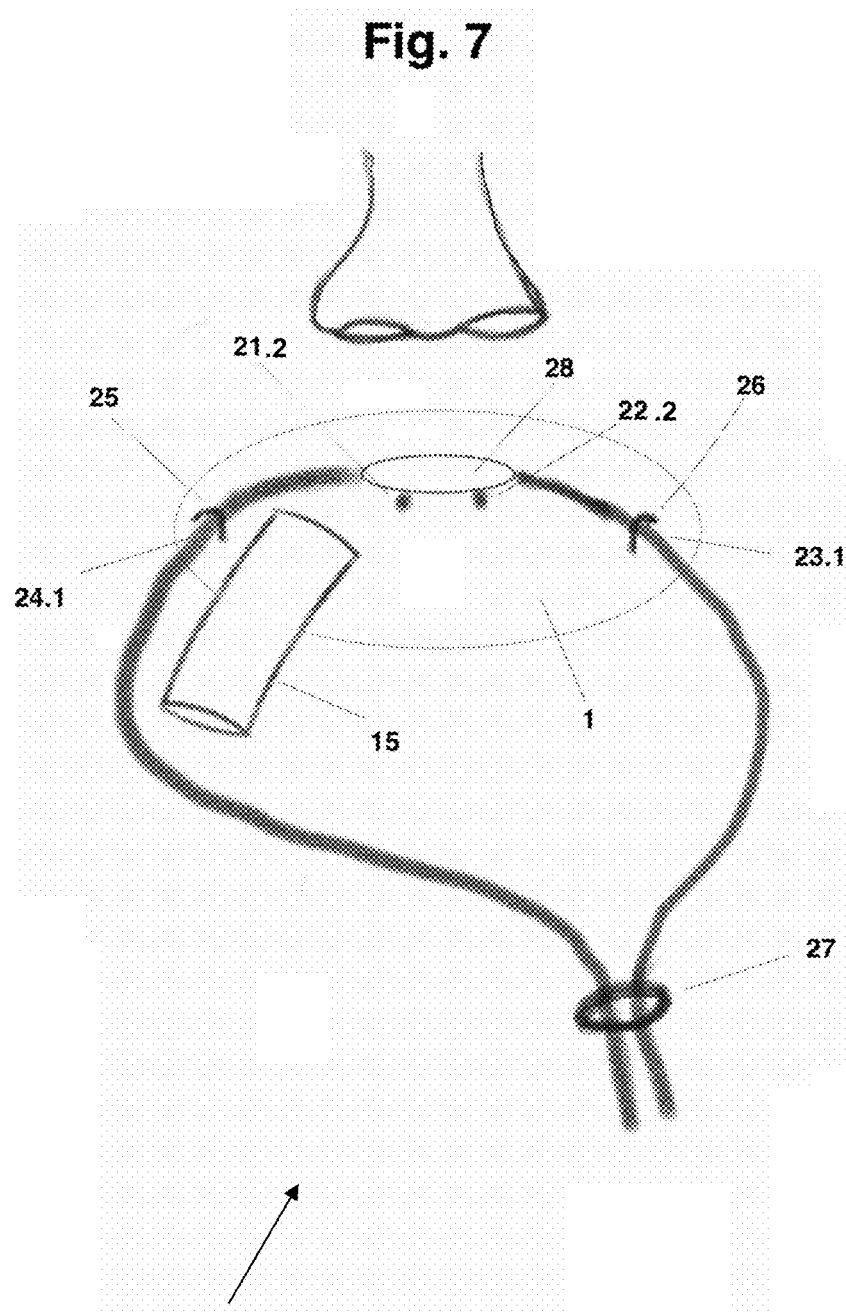

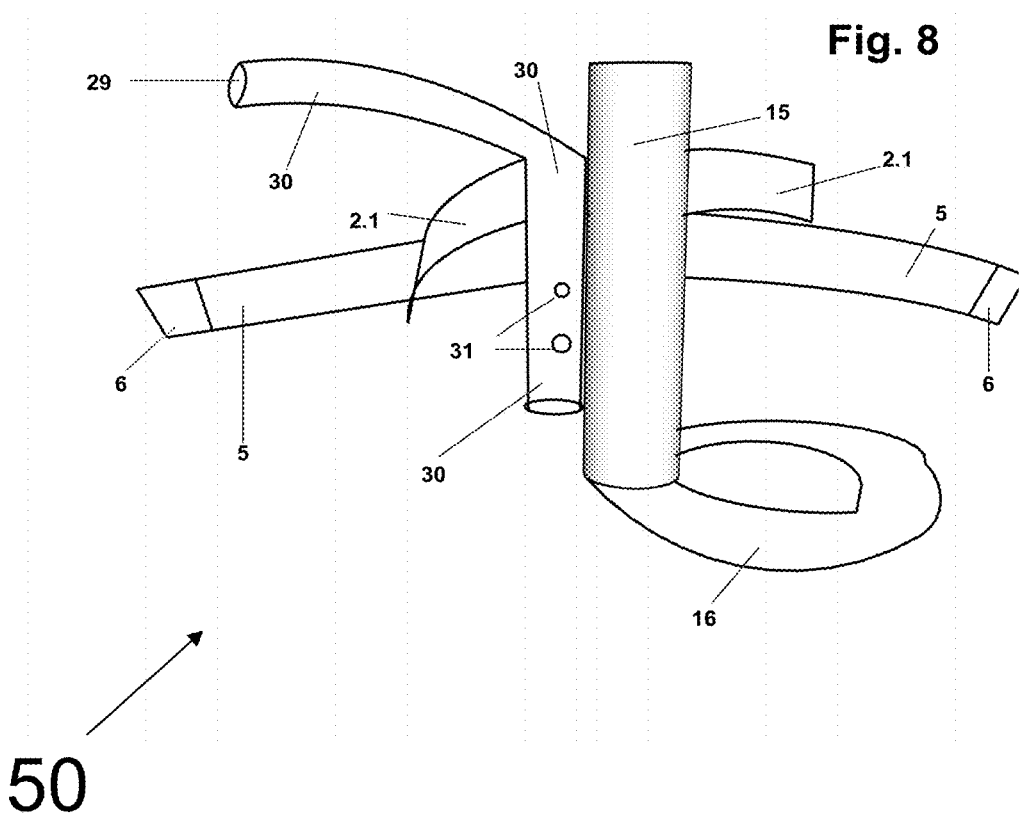

ANESTHETIC GAS SCAVENGING AND SANITARY BREATHING TUBE SECURING DEVICE

The present invention relates to an anesthetic gas scavenging and sanitary breathing tube securing device. Priority is claimed from provisional application Ser. No. 62/992,877, filed Mar. 20, 2020. Anesthetic gases are typically administered through a breathing tube inserted into the patient's airway. After insertion, a cuff around the breathing tube is inflated to allow positive-pressure ventilation and to prevent anesthetic gases from leaking into the operating room environment. The tube is then secured to the patient's airway, typically using adhesive surgical tape. This routine sequence of events, occurring in thousands of procedures each day, creates two potential problems.

BACKGROUND OF THE INVENTION

First, the gloved hand of the anesthesiologist is invariably exposed to the patient's oral secretions during tube insertion. These secretions may contain multiple contagious organisms, including influenza, herpes and coronaviruses, as well as a variety of bacterial species. The contaminated gloved hand may transfer these organisms to a roll of surgical tape when securing the tube to the patient's mouth and taping the eyes closed. Multiple studies have documented pathogenic microbial organisms contaminating rolls of tape in the intensive care setting as well as in the operating room. Since a typical roll contains in excess of 12 yards of tape and is repeatedly utilized, dozens of patients may be exposed to these infectious organisms from each roll. Guidelines and recommendations have been proposed to address this issue, including discarding the first section of dispensed tape, utilizing single-use rolls of tape, or tearing off a segment of tape prior to intubation. However, these strategies have been met with low compliance rates.

A second problem involves detectible concentrations of anesthetic gases, which may leak, often in significant amounts, around the breathing tube cuff and into the ambient air of the operating room. Inhalation of low levels of anesthetic gases may adversely affect the performance of operating room personnel during surgical procedures. Serious health risks from long-term exposure have been documented, including reduced fertility, spontaneous abortion, and neurologic, renal and liver disease. Aerosolized secretions containing infectious agents may also be dispersed from the airway in this fashion and into the operating room.

Regulations and technology have been developed to address this problem as well. However, the required anesthetic scavenging system built into modern anesthesia machines only removes excess anesthetic gases inside the closed breathing circuit. The inflatable cuffs on both an endotracheal tube and supraglottic airway are designed to prevent leakage of gas outside the circuit and into the ambient air. However, the higher cuff pressures required to ensure an adequate seal are associated with sore throat, laryngospasm and coughing on emergence from anesthesia. Longer exposure to high cuff pressures may have more severe consequences, including laryngeal nerve and mucosal ischemia. For these reasons, cuffs are often kept at low inflation pressures or left deflated during long cases. Significant levels of leaking anesthetic gases, as well as aerosolized particles, leaking around the cuff and out of the patient's airway may result, particularly when positive end expiratory pressure (PEEP) is utilized.

The invention described herein solves both of these problems by providing a means for securing the breathing tube with a single-use sanitary device, which also scavenges and eliminates leaking anesthetic gases as they emerge from the patient's airway.

SUMMARY OF THE INVENTION

The present invention relates to an anesthetic gas scavenging and sanitary breathing tube securing device. The present invention includes the following interrelated objects, aspects and features:

(1) The present invention provides a sanitary device, means and method for securing a breathing tube to the patient while simultaneously evacuating leaking anesthetic gases and aerosolized particles as they emerge from the airway.

(2) An airway-sized covering is provided with a plurality of accessible portals sized to receive a breathing tube shaft. In one embodiment, the accessible portals are fashioned with radially perforated tear lines which, when torn open, allow passage of the breathing tube shaft.

(3) After the patient is intubated, the covering is applied over the shaft of the breathing tube through the accessible portal. The device is then slid downward over the breathing tube shaft onto the patient's airway, which includes the mouth or both the mouth and nose. As this occurs, the torn perforations reveal novel adhesive triangular tabs. These tabs flip upward as the device is lowered over the shaft, adhering to the breathing tube once in place over the airway.

(4) An attached adhesive strip is provided adjacent to the accessible portal, allowing for additional fixation of the breathing tube shaft to the device. The covering, with fixed breathing tube, is secured to the patient using attached side adhesive strips or an attachable strap around the neck. All adhesive surfaces, including the accessible portals, are provided with peel-away backings to facilitate application, similar to a Band-Aid® strip.

(5) The under-surface of the airway covering is fashioned with suction tubing positioned circumferentially around the mouth. A plurality of holes in the suction tubing are directed centrally toward the mouth opening, with several holes directed toward the nasal openings. The distal end of the suction tubing is attached to the anesthesia machine's suction system or the waste anesthesia gas disposal port. As leaking anesthetic gases emerge from the patient's airway, the airway cover prevents dissipation into the operating room and the gases are evacuated by the suction tubing.

(6) The entire device is provided in a sanitary state and in disposable packaging.

Accordingly, it is a first object of the present invention to provide an anesthetic gas scavenging and sanitary breathing tube securing device.

It is a further object of the present invention to provide such a device which includes an airway-sized covering provided with a plurality of accessible portals sized to receive a breathing tube.

It is a yet further object of the present invention to provide such a device that is provided with means for securing it to a patient.

It is a still further object of the present invention to provide such a device with securement consisting of, in a preferred embodiment, an adhesive strip.

It is a yet further object of the present invention to provide such a device associated with suction tubing used to prevent dissipation of leaking anesthetic gases and aerosolized particles into the operating room.

These and other objects, aspects and features of the present invention will be better understood from the following detailed description of the preferred embodiments when read in conjunction with the appended drawing figures.

BRIEF DESCRIPTION OF THE DRAWINGS

FIG. 7 shows the embodiment of FIG. 6, in which the nasal cannula is inserted in the predetermined openings in the airway cover and attached to hooks on the surface of the airway cover.

FIG. 8 shows a third embodiment of the inventive device which uses suction tubing placed inside the oral cavity for evacuation of leaking anesthetic gases.

SPECIFIC DESCRIPTION OF THE PREFERRED EMBODIMENTS

Figure 1:
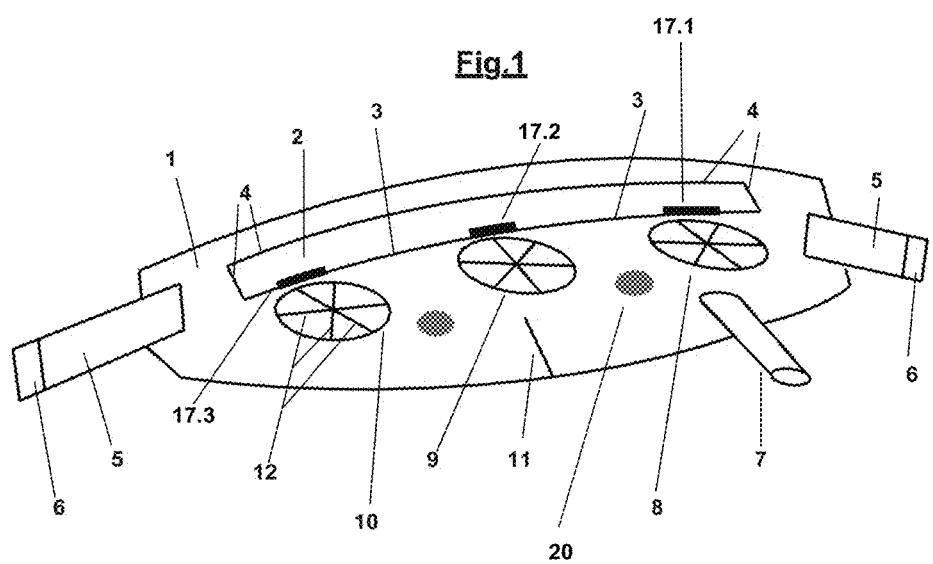
FIG. 1 shows a view of the top surface of the covering. An embodiment with three accessible portals with perforated tear lines is shown.

Reference is first made to FIG. 1. Therein, the top surface of the device 1 is shown. In this embodiment, the airway cover 1 has three accessible portals 8, 9 and 10. The accessible portals are shown in closed position with intact radially perforated tear-lines 12 that can be torn to open each portal. An adhesive strip 2 with non-stick backing is shown lying flat on the surface of the airway cover 1. The strip 2 is attached to the airway cover, using perforated, tearable segments 17.1, 17.2 and 17.3, each one adjacent to an accessible portal located along the interior edge 3 of the strip 2. The other edges 4 of the adhesive strip are not attached to the cover 1, allowing the strip 2 to flip upward as shown in FIGS. 3 and 4, and then wrap around the tube 15 once it is inserted in the airway.

Figure 2:
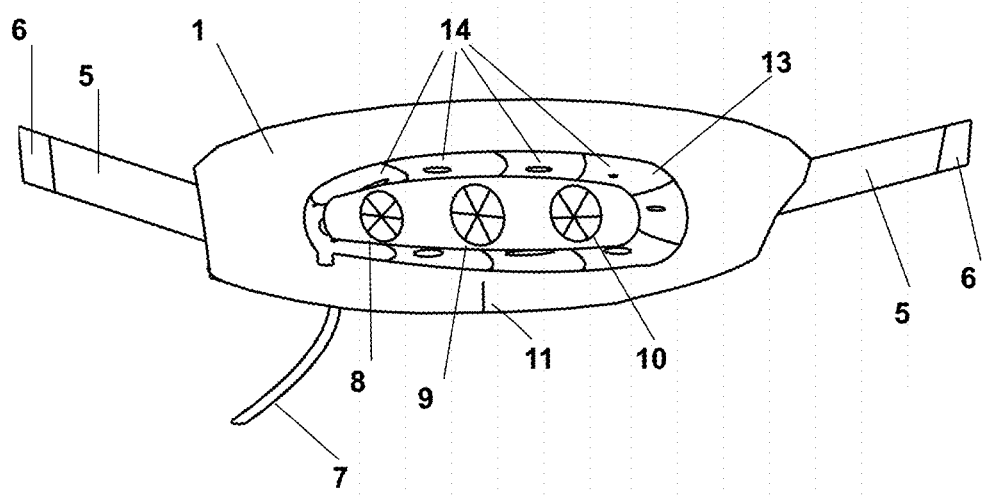
FIG. 2 shows the under surface of the covering.

The tip of the suction tubing 7 pierces through the airway cover 1 and the suction tubing 7 continues circumferentially as shown by reference numeral 13 in FIG. 2 around the portal and is attached to the under surface of the airway cover 1. Side adhesive strips 5 are shown on both sides of the airway cover, with non-adhesive tabs 6 for easy removal to expose adhesive. A center tearable crease 11 is provided to allow adjustments around the nostrils or nares, or to completely cover the nose of the patient as necessary. Several embodiments with different sizes and shapes of airway covers are disclosed herein, including airway covers enclosing the nasal openings as well as the mouth. Similarly, the course of the suction tubing may include the nasal opening as well in other embodiments.

With further reference to FIG. 2, the under surface of the airway cover 1 shows the suction tubing 13 circumferentially placed around the intended mouth opening. A plurality of small holes 14 in the suction tubing are oriented centrally to capture leaking anesthetic gases emerging from the airway once the tip of the suction tubing 7 is placed on suction.

Figure 3:
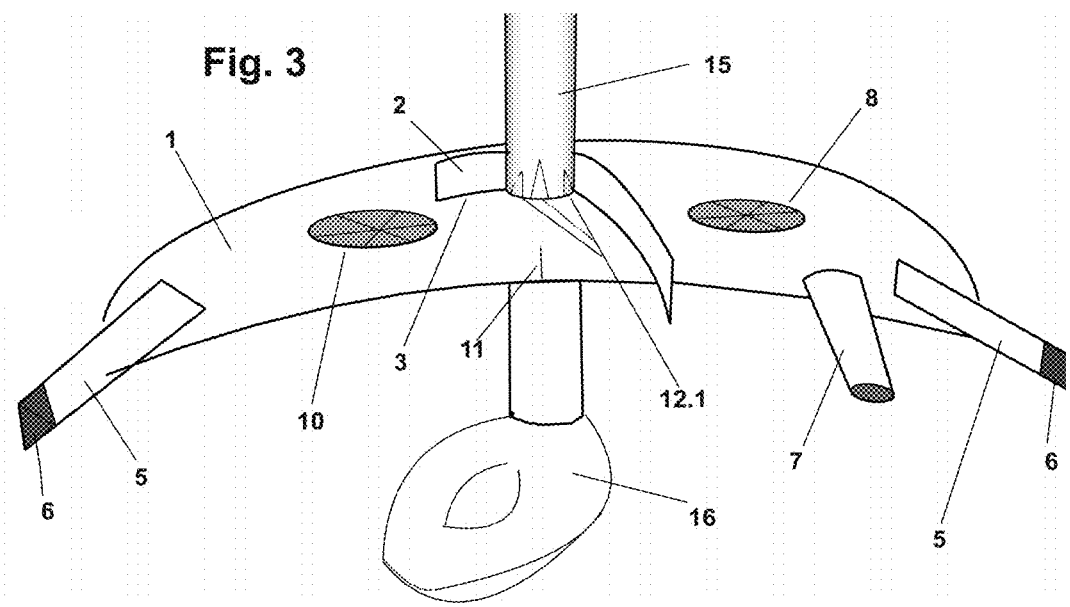
FIG. 3 shows the covering with a supraglottic airway tube inserted through the center accessible portal thereof.
Figure 4:
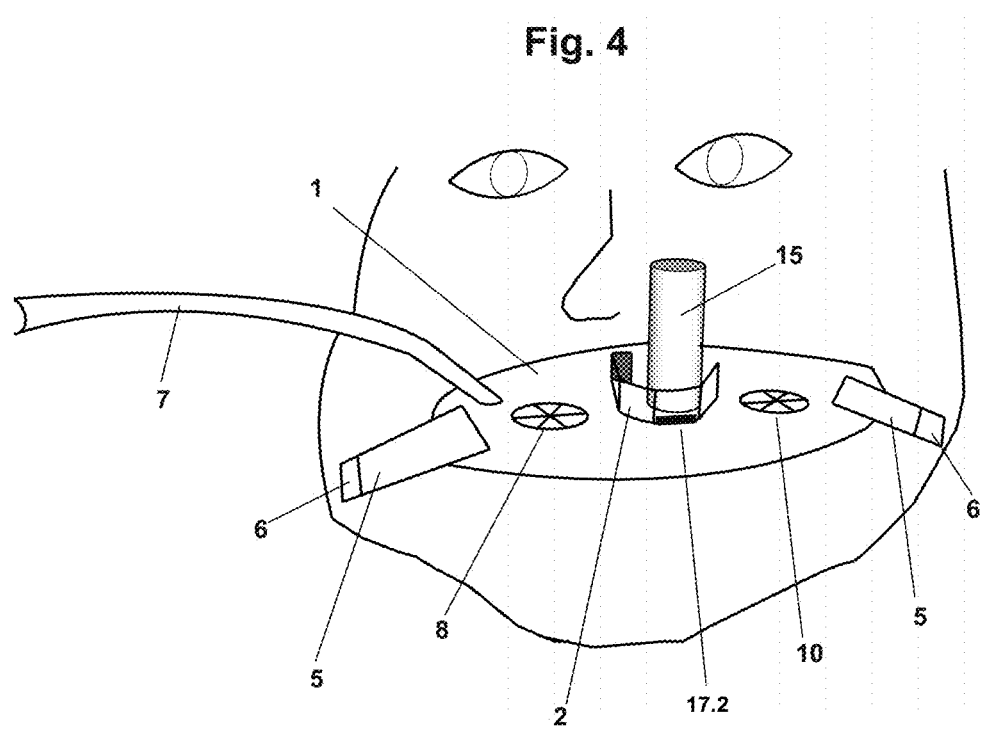
FIG. 4 shows the covering in position over the patient's airway.

With reference now to FIG. 3, a first embodiment of the inventive device 1 is shown using a supraglottic airway 16 of the patient. The tube 15 is inserted through the center accessible portal 9. The perforated tear lines 12 have been torn open, creating triangular flaps 12.1. The flaps have flipped upward as shown along the tube 15 as the device 1 is slid down onto the airway. The adhesive strip 2 has been flipped upward as shown and is shown wrapping around the tube 15 for additional fixation to the device 1.

In FIG. 4, the device 1 is shown in place over the airway of the patient with the adhesive strips 5 attached to the patient.

Figure 5:
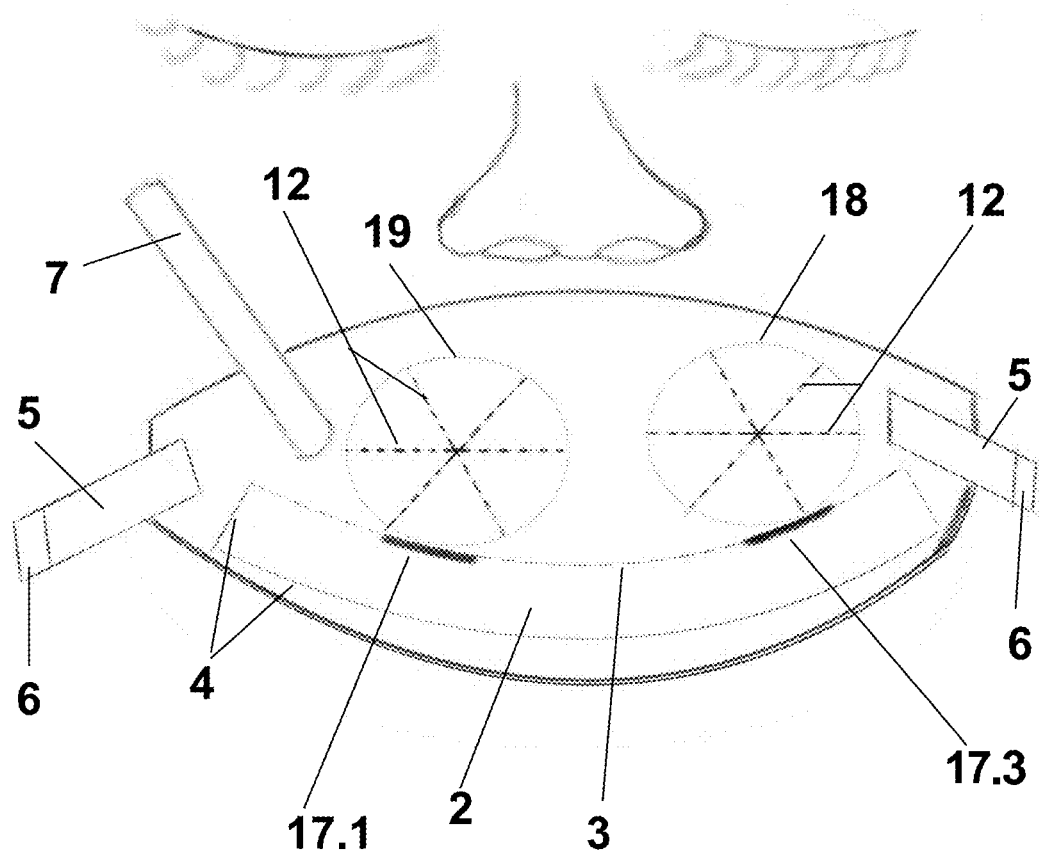
FIG. 5 shows the top surface of a first embodiment of the device with only two accessible portals and shown positioned over the airway of a patient.

FIG. 5 shows a further embodiment 31 showing only two accessible portals 18, 19. The radially perforated tear lines 12 are shown outlining the triangular flaps of the accessible portals. The adhesive strip 2 is shown attached to the airway cover along two perforated tearable segments 17.1, 17.3 on the interior edge 3. The perforated tearable segments 17.1, 17.3 are attached adjacent to the accessible portals 19 and 18, respectively.

Figure 6:
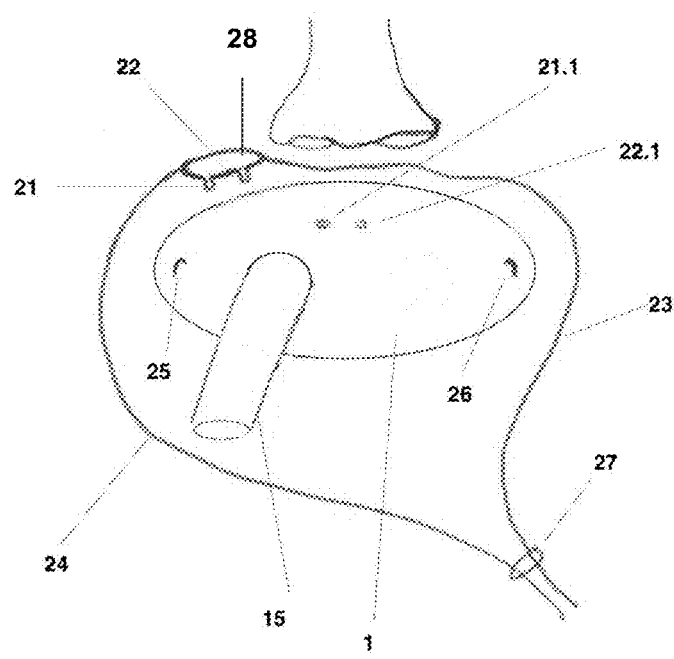
FIG. 6 shows a second embodiment of the inventive device with a single breathing tube portal, which utilizes a nasal cannula inserted into predetermined openings in the airway cover for suction.

FIG. 6 shows a further embodiment 40 in which the suction is provided by a standard nasal cannula 28, with the prongs 21, 22 inserted into predetermined openings 21.1 and 22.1 in the airway cover. The nasal cannula 28 tubing is attached to the airway cover 40 surface by an attachable means, in this embodiment, hooks 25 and 26 sized to press-fit the tubing as shown. The tubing continues around the patient's neck and tightened by standard nasal cannula means such as a movable elastic band 27.

In FIG. 7, the embodiment 40 of FIG. 6 is shown with the nasal cannula prongs 21, 22 inserted into their predetermined openings and the left and right nasal cannula tubing attached to their respective hooks 25, 26. The adjustable tightening means is an elastic band 27 around the tubing.

FIG. 8 shows a further embodiment 50 which eliminates the airway cover. Suction tubing for evacuation of leaking anesthetic gases and aerosolized particles extends into the oral cavity. The suction tubing 30 is secured to the patient in connection with the breathing tube 15 using sanitary adhesive tape 5. Other possible attachable means, such as a releasable clasp, may be utilized to connect the breathing tube and suction tubing together to the attachable means to the patient. The suction tubing and adhesive tape are provided as a single, integrated unit for easy application.

Many other variations are possible, such as an embodiment with a single large accessible portal, which extends across the entire airway. This would include a means for closing the portion of the accessible portal, which remains open after the tube, is placed. The size and shape of the airway cover may include both the nose and the mouth in some embodiments. The airway cover itself may contain an adhesive backing, eliminating the need for side adhesive strips or other attachable means. The airway cover is eliminated in another embodiment, in which adhesive tape alone is utilized with an attachable means to the breathing tube, such as a releasable clasp or adhesive tape extension. In this embodiment, suction tubing attached to the adhesive tape would be placed inside the mouth for evacuation of leaking gases and aerosolized particles as they collect orally. Other embodiments can include using a variety of different materials, including a plastic transparent mouth-cover to allow continuous monitoring for secretions. A further embodiment can include an airway cover with non-adhesive side strips with a detachable means, such as VELCRO®. These strips may secure the device to the face using an adjustable strap wrapped around the back of the patient's neck. Another embodiment can use a nasal cannula with the prongs inserted through predetermined openings on the surface of the airway cover, sized to receive nasal prongs. Suction can be applied to the nasal cannula, eliminating the need for suction tubing on the under surface of the airway cover. The nasal cannula tubing attaches to the airway cover by an attachable means, such as predetermined openings or slots in the airway cover to receive the nasal cannula tubing. The nasal cannula attaches the airway cover to the patient by tightening the nasal cannula tubing around the neck in the usual fashion. The device is designed to be generally inexpensive and may be manufactured from disposable materials, including biodegradable materials, such as pulp cardboard. Other materials, such as plastic may be utilized which permit sterilization and reuse. The device in its embodiments is flexible to permit it to conform to the mouth and surrounding face of the patient.

After intubation, the breathing tube 15 is generally positioned on the right side of the patient's mouth. However, the tube may be repositioned to the center or left side. The final location will determine which accessible portal 8, 9 or 10 on the embodiment of the device that is chosen will be utilized. In a right-sided tube placement, the anesthesiologist first removes non-adhesive backing on the undersurface of the right accessible portal 8. This portal 8 is placed over the distal open end of the breathing tube shaft 15 as it extends out of the patient's airway. The device 1, for example, is pushed down over the shaft 15, which passes through the right accessible portal 8, causing tearing along the perforated tear lines 12 (FIG. 3). The triangular flaps 12.1 are formed from tearing of the radially perforated tear lines. The triangular flaps 12.1 flip upwards along the tube shaft 15 as the device is slid downward into position over the airway. The suction tubing 13 (FIG. 2), attached to the undersurface of the airway cover 1, rests circumferentially around the airway. The holes 14 of the suction tubing (FIG. 2) are oriented centrally toward the airway opening. The flexibility of the suction tubing 13, as well as its attachment to the undersurface of the airway cover 1, creates a closed space over the patient's airway once the device 1 is attached to the patient. This prevents dissipation and escape of leaking anesthetic gases and aerosolized particles and facilitates removal by the suction tubing 13. Once in place over the airway, the adhesive triangular flaps 12.1 are manually pressed against the breathing tube shaft, securing the tube to the airway. The tube adhesive strip 2 is flipped upward as shown in FIG. 3. The attached segments 17.2, 17.3, adjacent to the center and left portals, are manually torn free along their perforated tear lines. The tube adhesive strip remains attached to the airway cover at segment 17.1, adjacent to the breathing tube shaft 15 in the right accessible portal 8. The backing of the tube adhesive strip 2 is pealed off, revealing the adhesive surface. The tube adhesive strip 2 is then wrapped circumferentially around the breathing tube shaft over the triangular flaps as shown in FIGS. 3 and 4. This further fixes the breathing tube shaft to the airway cover. The right and left side adhesive strips 5 are attached to the face of the patient after their backings are peeled off, securing the entire device 1 with attached breathing tube shaft 15 to the patient. The tip of the suction tube 7 is attached to the operating room suction or the waste anesthesia gas disposal system (not shown). If desired, a filter may be inserted at this attachment to absorb anesthetics and remove aerosolized particles, such as activated carbon. The tearable center crease 11 (FIGS. 1-3) allows expansion of the device to cover the nose as necessary. The unused accessible portals, in this embodiment the left 9 and center 10 accessible portals, may be used to access the airway for suctioning as needed. A pressure relief flap valve 20 is provided, similar to a non-rebreathing facemask, to prevent excessive negative pressure under the airway cover from the suction.

As the patient emerges from anesthesia, the non-adhesive tabs 6 allow easy removal of the side adhesive strips 5 by gripping them and pulling up. Alternatively, releasing the detachable neck straps in other embodiments allows removal of the device. The breathing tube 15 is removed from the airway for disposal with the device attached.

In another embodiment shown in FIGS. 6 and 7, leaking anesthetic gases are evacuated by a standard nasal cannula 28 placed on suction in the following manner: The two nasal prongs 21, 22 (FIG. 6) of the nasal cannula 28 are inserted into the airway cover through two predetermined openings 21.1, 22.1 on the outer surface of the airway cover, sized to tightly receive the nasal prongs. The two nasal prongs are pointed downward through the openings 21.1, 22.1 into the space under the airway cover 40. The two nasal prongs 21, 22 are situated centrally over the airway. The left and right nasal cannula tubing 23, 24 extend to the left and right, respectively, away from the nasal prongs on the outside of the airway cover. The left and right nasal cannula tubings are attached to the outer surface of the airway cover by provided means. Many such attachable means are available, such as, for example, hooks 25, 26 sized to clasp the nasal cannula tubing on the outer surface of the airway cover (FIGS. 6 and 7), an adhesive means, a snap, clip, VELCRO® fastener, or predetermined slots in the edge of the airway cover. The nasal cannula tubing 23 then continues around the patient's neck and tightened by sliding the band 27. The entire device, including airway cover with fixed breathing tube and inserted nasal cannula is held in place by tightening the nasal cannula tubing around the patient's neck. This involves sliding the adjustable band 27 around the nasal cannula tubing up to the back of the patient's neck as per usual nasal cannula operation. Suction is then applied to the nasal cannula to evacuate leaking anesthetic gases and aerosolized particles under the airway cover. At the end of the procedure, the nasal cannula is detachable from the airway cover and can be used during transport and in the recovery room to administer oxygen to the patient. In this embodiment, the suction tubing on the undersurface of the airway cover is eliminated.

As such, an invention has been disclosed in terms of preferred embodiments thereof, which fulfill each and every one of the objects of the invention as set forth hereinabove, and provide a new and useful anesthetic gas scavenging and sanitary breathing tube securing device of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. An airway cover, comprising:
  a) a flexible body sized to cover a mouth of a patient;
  b) a plurality of portals on said body defined by tearable score lines which, when torn, create an opening at a location of each portal;
  c) attachment means for attaching the flexible body over said mouth;
  d) each portal sized to receive a breathing tube attached to said cover;
  e) a suction tube attached to said cover and including a portion surrounding said portals, said portion including a plurality of holes adjacent said portals, said suction tube provided to suck away ambient atmosphere adjacent said cover through said holes; and f) a securing strip mounted on said cover for securing a breathing tube within one of said portals, said securing strip lying flat on said body and able to be lifted away from said body to facilitate securing said breathing tube to said cover, said securing strip being secured to said cover by a plurality of tearable segments, each tearable segment being located adjacent a respective one of said portals, at least one of said tearable segments, when torn, facilitating lifting said securing strip away from said body.

2. The airway cover of claim 1, wherein said plurality of portals comprises three portals.

3. The airway cover of claim 1, wherein said securing strip is coated on one side with an adhesive.

4. The airway cover of claim 3, wherein said securing strip is configured to wrap around a breathing tube inserted through one of said portals to secure said breathing tube to said cover.

5. The airway cover of claim 4, wherein said suction tube is attached to said cover surrounding said breathing tube.

6. The airway cover of claim 4, wherein said scored lines comprise three lines extending across each portal.

7. The airway cover of claim 6, wherein tearing said scored lines creates a plurality of triangular flaps that surround said breathing tube when inserted through a portal created by tearing said cover at said scored lines.

8. The airway cover of claim 3, wherein said at least one tearable segment comprises three segments, at least one of said tearable segments remaining untorn to keep said securing strip attached to said cover.

9. The airway cover of claim 1, wherein said suction tube is attached to said cover on an underside thereof adapted to be facing said mouth.

10. The airway cover of claim 9, wherein at least one of said holes through said suction tube comprises a lateral opening adapted to facilitate sucking ambient atmosphere away from said mouth.

11. The airway cover of claim 10, wherein said ambient atmosphere includes anesthetic gas and aerosolized particles.

12. The airway cover of claim 1, wherein said attachment means comprises a pair of opposed adhesive-backed strips.

13. The airway cover of claim 1, wherein a tearable crease is provided on said flexible body which when torn facilitates accommodation of said cover to faces of differing configurations.

14. An airway cover, comprising:
a) a flexible body sized to cover a mouth of a patient;
b) a plurality of portals on said body defined by tearable score lines which, when torn, create an opening at a location of each portal;
c) attachment means for attaching the flexible body over said mouth;
d) each portal sized to receive a breathing tube;
e) a suction tube attached on an underside of said cover and including a portion surrounding said portals, said portion including a plurality of holes adjacent said portals, said suction tube provided to suck away ambient atmosphere adjacent said cover through said holes, said ambient atmosphere including anesthetic gas and aerosolized particles;
f) a securing strip mounted on said cover for securing a breathing tube within one of said portals;
g) said securing strip being configured to wrap around a breathing tube inserted through one of said portals to secure said breathing tube to said cover, said securing strip being secured to said cover by a plurality of tearable segments, each tearable segment being located adjacent a respective one of said portals, at least one of said tearable segments, when torn, facilitating lifting said securing strip away from said body.

15. The airway cover of claim 14, wherein said securing strip is coated on one side with an adhesive.

16. The airway cover of claim 14, wherein at least one of said tearable segments remains untorn to keep said securing strip attached to said cover.

\* \* \* \* \*